(12) United States Patent
Gregory et al.

(10) Patent No.: US 10,392,612 B1
(45) Date of Patent: Aug. 27, 2019

(54) METHOD OF PARTICULATE TRANSPORT VIA SMALL-SCALE MORPHOLOGY MATERIALS

(71) Applicants: Jessica M. Gregory, Butte, MT (US); Katie Hailer, Butte, MT (US); Marisa Pedulla, Butte, MT (US); Jack Skinner, Butte, MT (US)

(72) Inventors: Jessica M. Gregory, Butte, MT (US); Katie Hailer, Butte, MT (US); Marisa Pedulla, Butte, MT (US); Jack Skinner, Butte, MT (US)

( * ) Notice: Subject to any disclaimer, the term of this patent is extended or adjusted under 35 U.S.C. 154(b) by 86 days.

(21) Appl. No.: 15/166,192

(22) Filed: May 26, 2016

Related U.S. Application Data

(60) Provisional application No. 62/166,392, filed on May 26, 2015.

(51) Int. Cl.
  *C12N 11/04* (2006.01)
  *C12N 7/00* (2006.01)
  *C12N 11/08* (2006.01)

(52) U.S. Cl.
  CPC ............... *C12N 11/04* (2013.01); *C12N 7/00* (2013.01); *C12N 11/08* (2013.01)

(58) Field of Classification Search
  None
  See application file for complete search history.

(56) References Cited

U.S. PATENT DOCUMENTS

2005/0106211 A1\* 5/2005 Nelson ..................... A61K 9/70
  424/423

\* cited by examiner

*Primary Examiner* — Jeffrey D Washville
(74) *Attorney, Agent, or Firm* — Haffey Vap PLLC; Mitchell J. W. Vap

(57) ABSTRACT

Small scale morphology materials transport particles and viruses from within the material to a living or non-living surface or artificial representation thereof. These materials are polymer composite and have features or are measured in their entirety to be less than 100 microns.

8 Claims, 6 Drawing Sheets

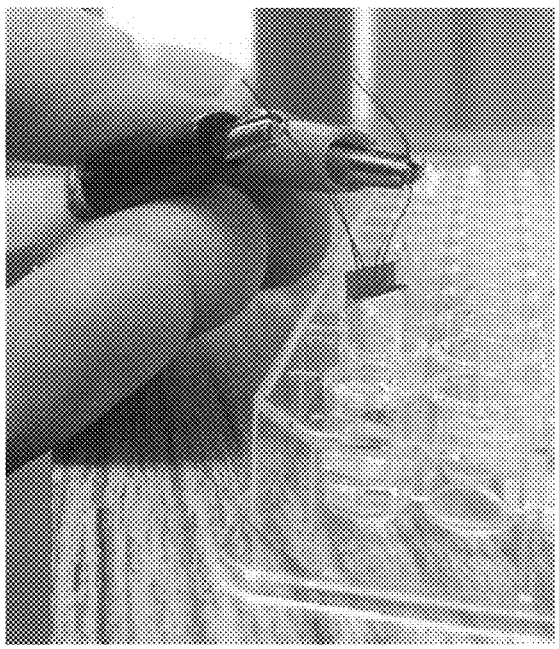
FIG. 3A
FIG. 3B

METHOD OF PARTICULATE TRANSPORT VIA SMALL-SCALE MORPHOLOGY MATERIALS

CROSS-REFERENCE TO RELATED APPLICATIONS

This application claims the benefits of U.S. Provisional Application No. 62/166,392, filed May 26, 2015, the disclosure of which is hereby incorporated by reference in its entirety including all figures, tables and drawings.

STATEMENT REGARDING FEDERALLY SPONSORED RESEARCH OR DEVELOPMENT

This invention was made with government support under EAGER GRANT #1338478 awarded by the National Science Foundation. The government has certain rights in this invention.

THE NAMES OF THE PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

Targeted delivery has allowed man to manipulate life on a cellular level. Life-saving chemotherapy and radiation can be delivered to diseased cells while sparing healthy cells. Genes can be manipulated within a cell by the intra-cellular delivery of bacteriophages and vectors. Antibiotic and vaccine delivery can be enhanced by delivering drugs to a cell with an adjuvant.

While methods of transporting and delivering these particles to a cell is ever evolving there remains a need for transport methods and materials that efficiently and effectively deliver particulate material to cells.

All patents, patent applications, provisional patent applications and publications referred to or cited herein, are incorporated by reference in their entirety to the extent they are not inconsistent with the teachings of the specification.

BRIEF SUMMARY OF THE INVENTION

The invention involves particle delivery via small-scale morphology materials, wherein the small-scale morphology materials have micro- or nano-scale features and/or are of micro- or nano-size entirely. The small scale morphology materials are of partial or complete synthetic nature, are made up in part or completely of polymer and/or polymer composite, and fabricated for the purpose of particulate delivery, movement, transfer, transport, or release from either the external or any more interior material surface to either living or non-living systems or artificial representations thereof.

BRIEF DESCRIPTION OF THE SEVERAL VIEWS OF THE DRAWING

FIG. 3A is a photograph showing release of a particulate from a preferred embodiment of the small-scale morphology material of the subject invention by ohmic heating and melting of the material to release particles.

FIG. 3B is a photograph showing completed release of a particulate from the preferred embodiment of the small-scale morphology material.

DETAILED DESCRIPTION OF THE INVENTION

The invention involves small-scale materials which facilitate either passively or by external manipulation the transport of particles from the material to living or non-living systems. The small scale morphology materials of the subject invention are of partial or complete polymer and/or polymer composite composition and may contain multiple materials. Features of these materials or the materials in their entirety are less than 100 micron in at least one dimension.

The small-scale morphology materials of the subject invention are micro- and nano-scale size materials or have either micro- and/or nano-scale features. Micro- or nano-scale refers the materials or features being from about 0 to about 100 microns and less than about 100 microns. Size refers to either diameter, and/or circumference, and/or perimeter, and/or volume of the subject material or of a material feature.

The small scale morphology materials of the subject invention can either comprise components or be comprised entirely of fiber/s or transport vesicle/s or vessel/s or transport particle/s or a combination thereof including a combination with or without fibers. The subject materials can be made as a single layer, multiple layers, a composite, or be a colloid. The micro- and/or nano-scale materials can have organic and/or inorganic components or can be of an entire synthetic composition by way of either construction, and/or fabrication, and/or chemical synthesis, and/or preparation, and/or assembly. These micro- and/or nano-scale materials can likewise be of partial or complete polymer and/or polymer composite material. The synthetic nature of small scale morphology materials are either fabricated, and/or chemically synthesized, and/or prepared, and/or assembled. It is noted however that not all components of these materials may be of synthetic nature and materials may contain a combination of synthetic and organic, or non-synthetic, materials.

Figure 1A:
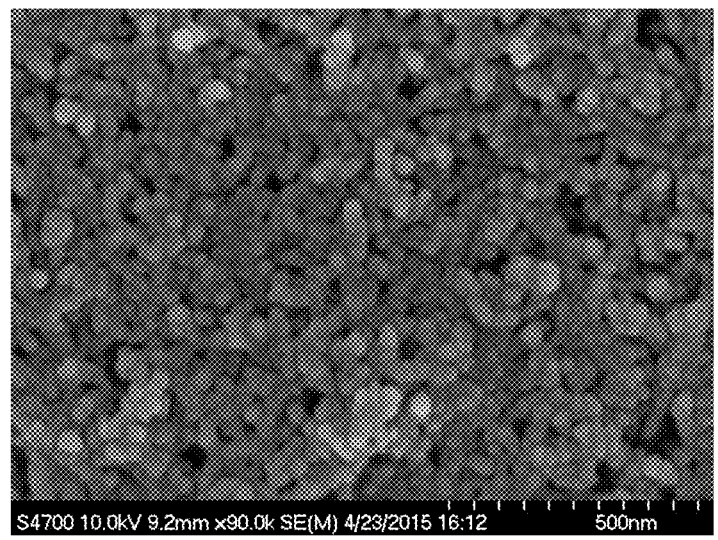
FIG. 1A is a scanning electron micrograph of a particulate that could be transported via the small-scale morphology material of the subject invention.
Figure 1B:
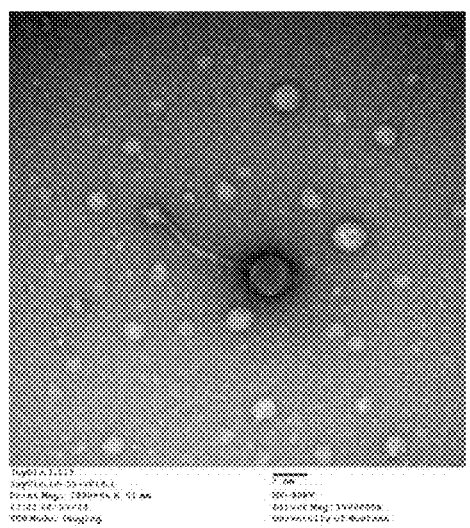
FIG. 1B is a transmission electron micrograph of virus that could be transported via the small-scale morphology material of the subject invention.
Figure 2A:
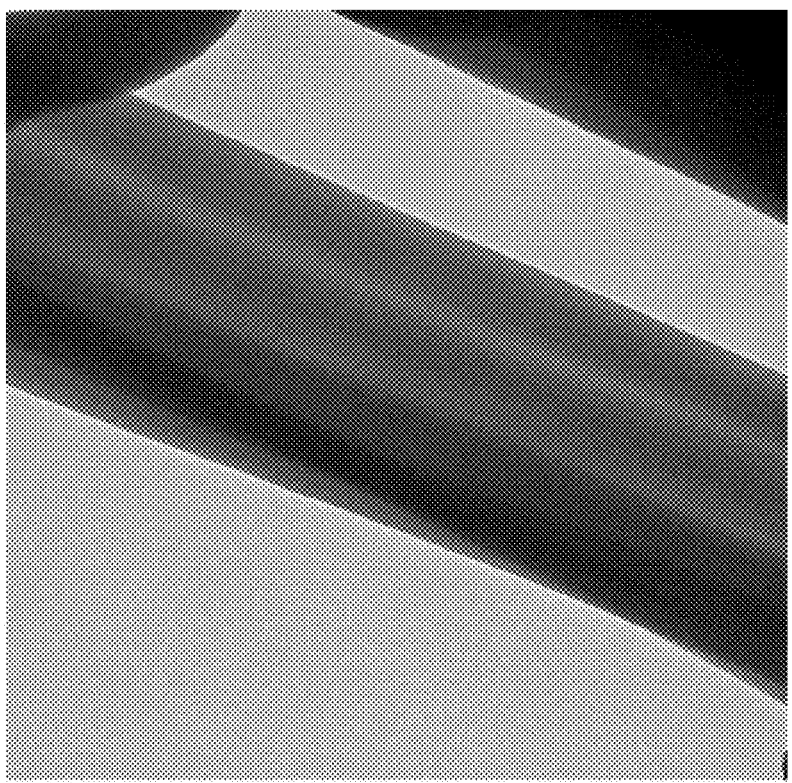
FIG. 2A is a transmission electron micrograph of a preferred embodiment of the small-scale morphology material of the subject invention that are coaxial or core-sheath fibers.
Figure 2B:
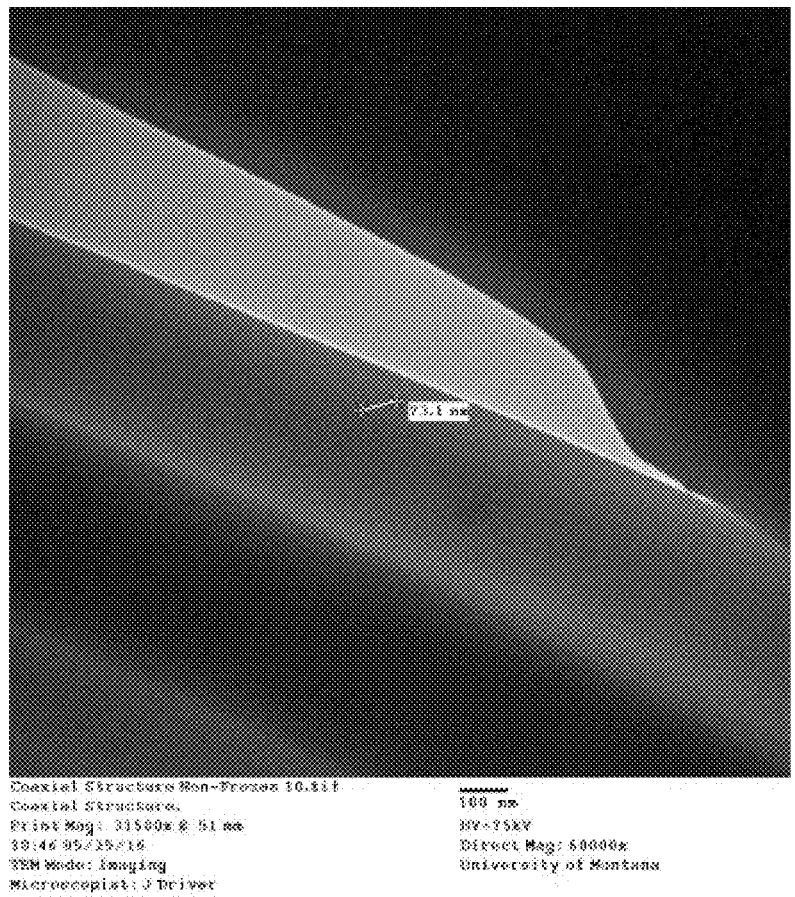
FIG. 2B is a transmission electron micrograph of the preferred embodiment of coaxial or core-sheath fibers containing a virus.
Figure 2C:
FIG. 2C is the transmission electron micrograph of FIG. 3B of coaxial or core-sheath fibers containing a virus at a lower magnification.
Figure 4A:
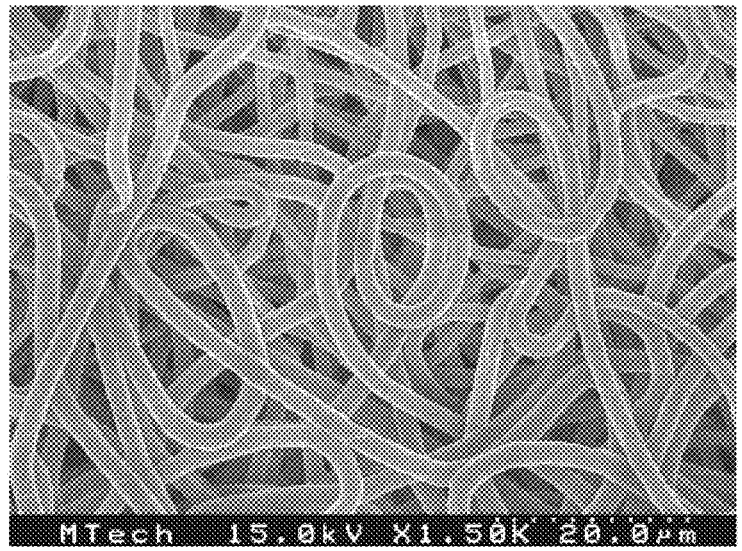
FIG. 4A is a scanning electron micrograph of another preferred embodiment of the small-scale morphology material of the subject invention that is non-coaxial or core-sheath.
Figure 4B:
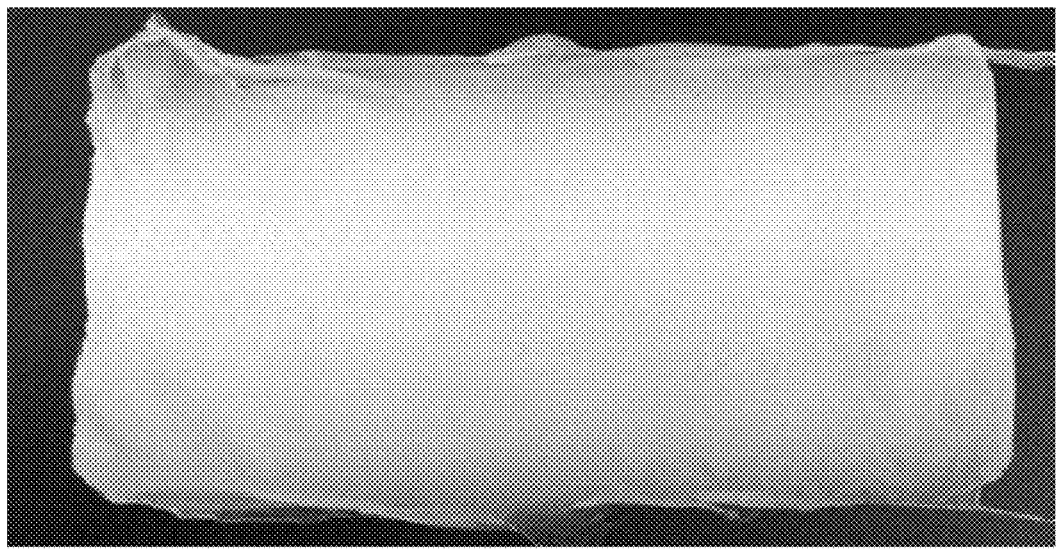
FIG. 4B is a photograph showing fibers from FIG. 4A on a macro scale that can be used to deliver particles or virus as the small-scale morphology material of the subject invention.

Preferred embodiments of the subject small-scale morphology materials of the subject invention are shown in FIGS. 2A-C and 4A-B. Small scale morphology materials may take on various structure seen in FIG. 2A (core-sheath fibers) versus FIG. 4A (single material fibers) and components may be oriented randomly or aligned or placed in a manner conducive to particle delivery. FIG. 2A-C show a micro size polymer fibers with a core-sheath structure. A single fiber polymer shell casing 10 has a microfluidic channel 12 inside. Fibers were fabricated using coaxial electrospinning. The microfluidic core carries particles 16 (FIGS. 1A and 1B) to be released.

The small scale morphology materials of the subject invention are for either the general, and/or intended, and/or specific delivery, movement, transfer, transport, or release of either particles, and/or particulate, and/or viruses. Particles can include, but are not limited to, molecules, viruses, and natural or synthetic materials. Particles may be released to a living organism, innate surface, or artificial representation of either of these.

Particle/s and/or virus delivery from small scale morphology materials of the subject invention can be released from either the material matrix, and/or material surface, and/or material core. In the case that particles, and/or particulate, and/or viruses are delivered from a material core. The core refers to any layer more interior to that of the surface of the material which carries particles, and/or particulates, and/or viruses for delivery and can be of a material which differs from that found on the material surface or any layer more interior to the surface material. Particles for delivery via small scale morphology materials can be attached to fibers chemically, electrostatically, mechanically, or physically. Particles for delivery via small scale morphology materials may be released via active (with added energy) or passive means (without added energy). Particles for delivery via small scale morphology materials may be released immediately, or slowly over time, or a combination of these. More than one type of particle, either in composition, synthesis, chemistry, assembly, or appearance can be delivered via small scale morphology materials of the subject invention.

Small scale morphology materials used for either the transfer, transport, movement, delivery, or release of either particles, and/or particulate, and/or viruses, can consist of more than one material or of a single material. In the case that small scale morphology materials consist of more than one material, materials can differ in either chemical makeup, and/or consistency, and/or viscosity, and/or conductivity, and/or ion transfer ability, and/or amount.

Particles, and/or particulate, and/or viruses, and/or molecules, released from the subject material can be used for the treatment of disease, treatment of pain, sterilization of surfaces, manipulation of surface properties, filtration, energy harvesting, alteration of mechanical properties, adhesives, repellents, vaccines, preventative therapeutics, long-term implantation in eukaryotic organisms, manipulation of living system interactions, alteration of biological functions or processes, antibacterial agents, sensors, light manipulation, cosmetics, general and relaxation therapies, and cloak or disguise purposes.

Particles for release into living or non-living systems is carried out by small scale morphology materials of the subject invention. Particles can be attached to fibers via electrostatic, chemical, mechanical, or physical means and are released via energy requiring or passive means. Particles can include, but are not limited to, viruses and/or synthetic nanoparticles. When particles are embedded within a polymer material and are of other composition, the material is referred to as doped. Specifically, nanoparticle doped polymer fibers nanoparticles mixed in with the polymer melt or polymer mixed in solvent, and are then fed to a fabrication device such as an electrospinner for fiber construction. Resultant fibers would contain a polymer matrix but with nanoparticles of non-polymer origin as well. In the embodiment shown in FIG. 2A-C, where coaxial fibers were constructed for the purpose of virus delivery. Coaxial electrospinning in this case, created a polymer sheath with water-based core for maintenance of the virus to be delivered for antibacterial purposes. A combination of both of these examples could incorporate nanoparticle into polymer solution used for the protective sheath, and also contain virus in fluid as the fiber core material for nanoparticle assisted antibacterial treatment delivery.

One or more particles are associated with the material of the subject invention. These particles can be attached to the exterior of small scale morphology materials, be contained within the small scale morphology material matrix, be contained within any layer more interior to the material surface, or be contained within a microfluidic channel.

Small scale morphology materials of the subject invention serve as delivery vehicles for particles from the material to living or non-living systems, or artificial representations of either of these. The subject material can move viruses in combination with or without nanoparticles from a polymer material to a living person for the purpose of antibiotic treatment. Nanoparticles in this case and in the case of other particulate release can serve as an adjuvant which enhances particle delivery and/or effectiveness upon successful transfer from small scale morphology materials to the intended living or non-living system, or artificial representation of these systems.

EXAMPLE 1-Material Preparation

The small-scale morphology material of the subject invention can be fabricated using electrospinning technique. Electrospinning involves delivery of a polymer melt or polymer dissolved in solvent solution to a capillary or needle held above or horizontal to a collection plate. Polymers suitable for creating the small-scale morphology material of the subject invention include, but are not limited to, polycaprolactone, polyvinyl alcohol, polyethylene oxide, polystryene, polyethylene oxide, PEDOT, PEDOT/PSS, polypropylene, and petadecylphenol. Voltage differential initiated between the tip of the capillary where polymer is being released and the collection plate surface creates a force which pulls the polymer solution or melt from the capillary tip, depositing micro- or nano-sized fibers or vesicles onto a collection plate.

The subject invention is meant to deliver particles; several methods may be used to equip these polymer delivery systems with particles for subsequent release: (1) particles can be pre-mixed with the polymer melt or polymer solution, (2) in the case of multiple layered materials such as core-sheath fibers created through coaxial electrospinning, particles may be incorporated into a core layer (See FIG. 2A-C), or any layer other than the outermost layer, or any combination of layers, (3) particles may be added post-process via soaking in a solution filled with particles, electrospraying particles onto electrospun materials, creating an adhesive layer and adding dry particles, etc, or any combination of these methods. Iron-doped hydroxyapatite, nanoparticles have been used to enhance bacteriophage antibacterial properties, (see, J. M. Andriolo et al., Iron-doped Apatite Nanoparticles for Improvement of Phage Therapy, Journal of Vacuum Science and Technology B, 32(6), 2010).

EXAMPLE 2-Particle Release

For subsequent delivery of particles from small scale morphology materials, several methods can be used. FIG. 4 demonstrates ohmic heating used to melt fibers for particle release. Melting of fibers or initiation of particle release from fiber surfaces can also be initiated externally using wireless charging devices, light, plasmonics, vibration, or magnetic sources or any source which alters material characteristics to allow for particle release. Upon release of particles, the material can itself dissolve into the living or non-living system for which it released to, or may be removed and discarded.

It is understood that the foregoing examples are merely illustrative of the present invention. Certain modifications of the articles and/or methods may be made and still achieve the objectives of the invention. Such modifications are contemplated as within the scope of the claimed invention.

The invention claimed is:

1. A method of transporting and releasing particles or virus to a system comprising the steps of:
   attaching at least one virus to a small-scale morphology material wherein a portion of the small-scale morphology material is comprised of polymer electrospun fibers further comprising coaxial fiber with a microfluidic core, wherein at least a portion of the coaxial fibers measures less than about 100 micrometers in diameter;
   contacting the small-scale morphology material to a living system; and
   releasing the at least one virus from the small-scale morphology material.

2. The method of claim 1, wherein said at least one virus is attached to said small-scale morphology material by a method selected from the group consisting of chemically, electrostatically, and mechanically.

3. The method of claim 1, wherein said at least one virus is attached to said material by being incorporated into the polymer matrix.

4. The method of claim 1, wherein said at least one particle is attached to externally to said material.

5. The method of claim 1, wherein said entire material measures less than about 100 micrometers in diameter.

6. The method of claim 1, wherein said material is a non-coaxial fiber.

7. The method of claim 1 where said virus is attached to the internal portion of said coaxial fiber.

8. The method of claim 1 where said virus is contained within said microfluidic core.

* * * * *